(12) United States Patent
Grashow et al.

(10) Patent No.: US 11,890,417 B2
(45) Date of Patent: *Feb. 6, 2024

(54) CRADLE CUSHION HAVING SIDE STABILIZERS

(71) Applicant: KONINKLIJKE PHILIPS N.V., Eindhoven (NL)

(72) Inventors: Jonathan Sayer Grashow, Cheswick, PA (US); Robert O'Grady, Pittsburgh, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 295 days.

This patent is subject to a terminal disclaimer.

(21) Appl. No.: 17/358,221

(22) Filed: Jun. 25, 2021

(65) Prior Publication Data

US 2021/0361898 A1 Nov. 25, 2021

Related U.S. Application Data

(63) Continuation of application No. 15/665,782, filed on Aug. 1, 2017, now abandoned, which is a
(Continued)

(51) Int. Cl.
*A61M 16/06* (2006.01)
*A61M 16/00* (2006.01)
*A61M 16/08* (2006.01)

(52) U.S. Cl.
CPC .... *A61M 16/0622* (2014.02); *A61M 16/0057* (2013.01); *A61M 16/06* (2013.01);
(Continued)

(58) Field of Classification Search
CPC .......... A61M 16/0666; A61M 16/0672; A61M 16/06; A61M 16/0605; A61M 16/0583
See application file for complete search history.

(56) References Cited

U.S. PATENT DOCUMENTS

| 5,117,818 A | 6/1992 | Palfy |
| 5,724,965 A | 3/1998 | Handke et al. |
| (Continued) | | |

FOREIGN PATENT DOCUMENTS

| CN | 101954130 A | 1/2011 |
| EP | 2130563 A1 | 12/2009 |
| (Continued) | | |

*Primary Examiner* — Margaret M Luarca
(74) *Attorney, Agent, or Firm* — Michael W. Haas

(57) ABSTRACT

A cradle style cushion includes a central sealing body portion including a front wall, a rear wall, a top wall and a bottom wall. The top wall includes a central sealing surface, a first stabilizing surface and a second stabilizing surface, the first and second stabilizing surfaces each extending upwardly and outwardly with respect to the central sealing surface and a top edge of the front wall and being structured to wrap around and engage an outside of the nostrils when the patient interface device is donned by the patient, wherein the first stabilizing surface includes a first front side edge portion and the second stabilizing surface includes a second front side edge portion, and wherein the top edge of the front wall, the first front side edge portion and the second front side edge portion together define a front opening of the central sealing body portion.

16 Claims, 13 Drawing Sheets

Related U.S. Application Data continuation of application No. 14/414,288, filed as application No. PCT/IB2013/055440 on Jul. 3, 2013, now Pat. No. 9,764,107.

(60) Provisional application No. 61/671,926, filed on Jul. 16, 2012.

(52) U.S. Cl.
CPC .... *A61M 16/0666* (2013.01); *A61M 16/0683* (2013.01); *A61M 16/0816* (2013.01); *A61M 2210/0618* (2013.01)

(56) References Cited

U.S. PATENT DOCUMENTS

| | | | |
|---|---|---|---|
| 5,931,854 | A | 8/1999 | Pillon |
| 9,095,673 | B2 | 8/2015 | Barlow |
| 2004/0226566 | A1 | 11/2004 | Gunaratnam |
| 2008/0047560 | A1 | 2/2008 | Veliss et al. |
| 2008/0060649 | A1 | 3/2008 | Veliss et al. |
| 2009/0044808 | A1 | 2/2009 | Guney |
| 2009/0120442 | A1 | 5/2009 | Ho |
| 2010/0000534 | A1 | 1/2010 | Koouj |
| 2010/0158136 | A1 | 6/2010 | Peng et al. |
| 2010/0229872 | A1 | 9/2010 | Ho |
| 2011/0000492 | A1 | 1/2011 | Veliss |
| 2011/0146685 | A1 | 6/2011 | Allan |
| 2011/0247627 | A1 | 10/2011 | Omura et al. |
| 2011/0265796 | A1 | 11/2011 | Amarasinghe |
| 2011/0315145 | A1 | 12/2011 | Beevers et al. |
| 2012/0067349 | A1 | 3/2012 | Barlow |
| 2012/0138060 | A1 | 6/2012 | Barlow |
| 2012/0266890 | A1 | 10/2012 | Baecke |
| 2013/0160772 | A1 | 6/2013 | Tabrizchi |
| 2013/0263860 | A1 | 10/2013 | Sofranko |
| 2013/0263861 | A1 | 10/2013 | Holtzapple |
| 2014/0283842 | A1 | 9/2014 | Middelkoop |

FOREIGN PATENT DOCUMENTS

| | | |
|---|---|---|
| JP | 2009545408 A | 12/2009 |
| JP | 2010512193 A | 4/2010 |
| JP | 2012526592 A | 11/2012 |
| JP | 2014530708 A | 11/2014 |
| JP | 2014534030 A | 12/2014 |
| RU | 2392010 C1 | 6/2010 |
| WO | 9904842 A1 | 2/1999 |
| WO | 2005076874 A2 | 8/2005 |
| WO | 2008019294 A2 | 2/2008 |
| WO | 2009139647 A1 | 11/2009 |
| WO | 2010131189 A1 | 11/2010 |
| WO | 2010139014 A1 | 12/2010 |
| WO | 2012040791 A1 | 4/2012 |
| WO | 2012055886 A1 | 5/2012 |
| WO | 2012061783 A1 | 5/2012 |
| WO | 2013057672 A1 | 4/2013 |
| WO | 2013066195 A1 | 5/2013 |

CRADLE CUSHION HAVING SIDE STABILIZERS

CROSS-REFERENCE TO RELATED APPLICATIONS

This present application is a continuation under 35 U.S.C. § 120 of U.S. patent application Ser. No. 15/665,782, filed on Aug. 1, 2017, which is a continuation of U.S. patent application Ser. No. 14/414,288, filed Jan. 12, 2015, which claimed priority to PCT application PCT/IB2013/055440 filed Jul. 3, 2013, which claims the priority benefit under of U.S. Provisional Application No. 61/671,926, filed on Jul. 16, 2012, the contents of which are herein incorporated by reference.

BACKGROUND OF THE INVENTION

1. Field of the Invention

The present invention pertains to patient interface devices structured to deliver a flow of breathing gas to a user, and, in particular, to a cradle style sealing cushion for a patient interface device that has side stabilizers providing an improved fit and seal.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of a patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

One type of known sealing cushion is called a cradle style sealing cushion. A cradle style sealing cushion is structured to rest beneath the patient's nose and provides an air-tight seal against the surfaces of the nasal septum and nostrils (and also possibly the upper lip). One major disadvantage of current cradle style sealing cushions is that the seal between the cushion and the nose is very sensitive to the alignment of the cushion to the nose. For this reason, many wearers find it difficult to maintain a reliable seal when using a mask with a cradle style sealing cushion due to misalignment caused by movement of the wearer or external forces acting on the mask (e.g. from a bed pillow). When the seal is broken, the ability of the respiratory therapy device to deliver adequate airflow to the wearer may be compromised. Additionally, air leakage may be directed into the wearer's face, causing discomfort.

SUMMARY OF THE INVENTION

Accordingly, it is an object of the present invention to provide a cradle style sealing cushion that overcomes the shortcomings of conventional cradle style sealing cushions. This object is achieved according to one embodiment of the present invention by providing cradle style sealing cushion that includes hat has side stabilizers providing an improved fit and seal.

In one embodiment, a cradle style cushion for a patient interface device is provided that includes a central sealing body portion defining an internal chamber, the central sealing body portion including a front wall, a rear wall, a top wall and a bottom wall. The top wall includes a central sealing surface structured to engage a septum and a bottom of each nostril of a patent (and possibly the portion of the patient's mouth above the upper lip) when the patient interface device is donned by the patient, a first stabilizing surface and a second stabilizing surface, the first and second stabilizing surfaces each extending upwardly and outwardly with respect to the central sealing surface and a top edge of the front wall in a direction away from the bottom wall and being structured to wrap around and at portions thereof engage an outer side (transverse to the bottom) of a respective one of the nostrils when the patient interface device is donned by the patient, wherein the first stabilizing surface includes a first front side edge portion and the second stabilizing surface includes a second front side edge portion, and wherein the top edge of the front wall, the first front side edge portion and the second front side edge portion together define a front opening of the central sealing body portion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
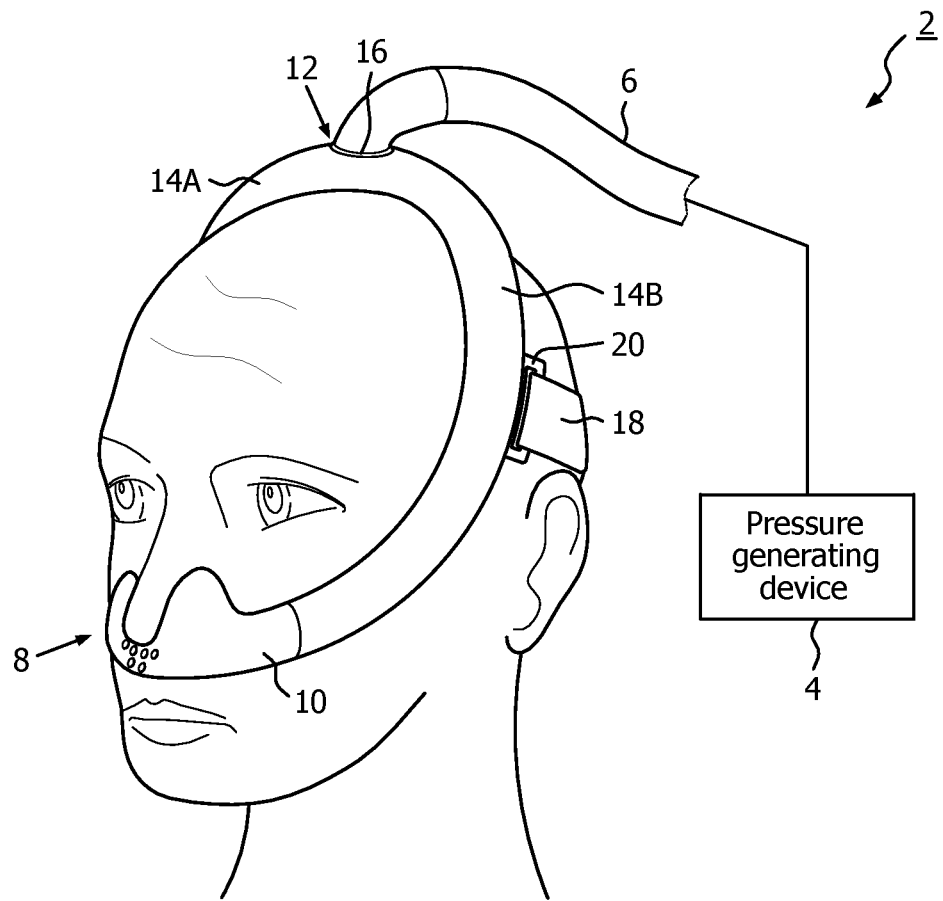
FIG. 1 is a schematic diagram of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the invention is generally shown in FIG. 1. System 2 includes a pressure generating device 4, a delivery conduit 6, and a patient interface device 8. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the exemplary embodiment, patient interface device 8 comprises a cradle style nasal mask structured to engage the nose of the patient and provide a seal against the surfaces of the nasal septum and nostrils (and possibly the portion of the patient's mouth above the upper lip) as described in detail herein. In the present embodiment, patient interface device 8 includes a cradle style sealing cushion 10 coupled to a tubing assembly 12. As seen in FIG. 1, tubing assembly 12 includes a first arm 14A structured to rest along a first side of the patient's head and a second arm 14B structured to rest along a second side of the patient's head when patient interface device 8 is donned by the patient. A first end of first arm 14A and a first end of second arm 14B are each fluidly coupled to cradle style sealing cushion 10. In addition, a second end of first arm 14A and a second end of second arm 14B are each fluidly coupled to a coupling connector 16 structured to rest on top of the head of the patient when patient interface device 8 is donned by the patient. Delivery conduit 6 is fluidly coupled to coupling connector 16 to allow the flow of breathing gas from pressure generating device 4 to be communicated to cradle style sealing cushion 10 through tubing assembly 12, and then, to the airway of a patient. Straps 18 of a headgear component are attached to first arm 14A and second arm 14B via attachment members 20 to secure patient interface device 8 to the patient's head.

Figure 2:
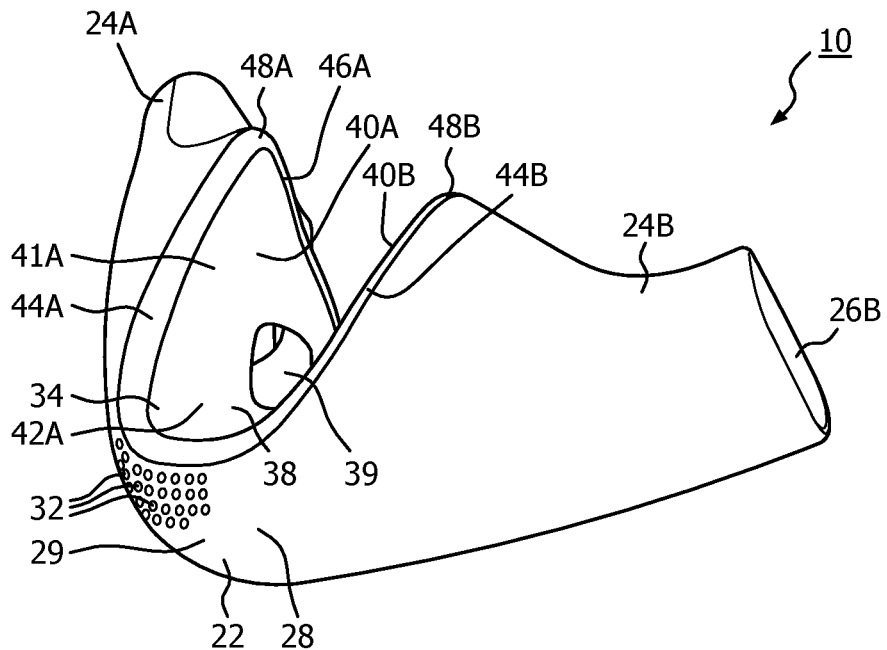
FIG. 2 is a front isometric view.
Figure 3:
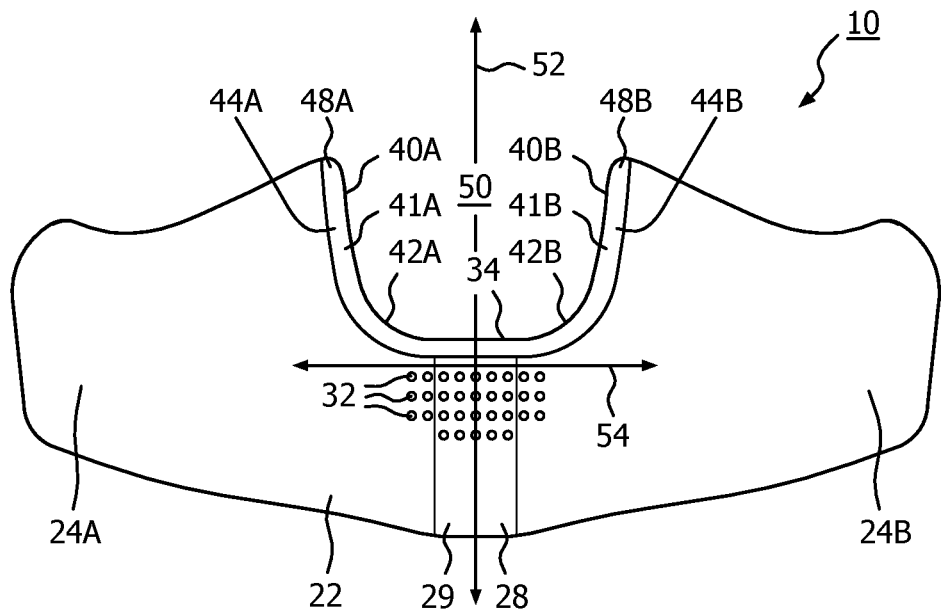
FIG. 3 is a front elevational view.
Figure 4:
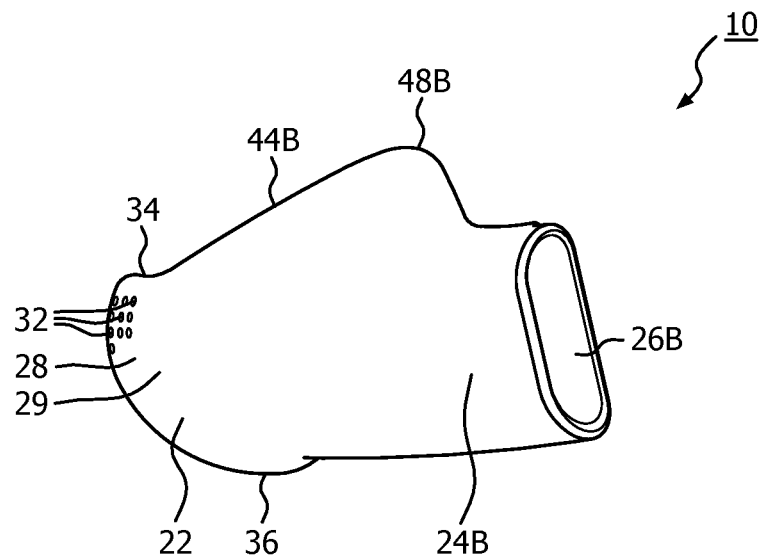
FIG. 4 is a side elevational view.
Figure 5:
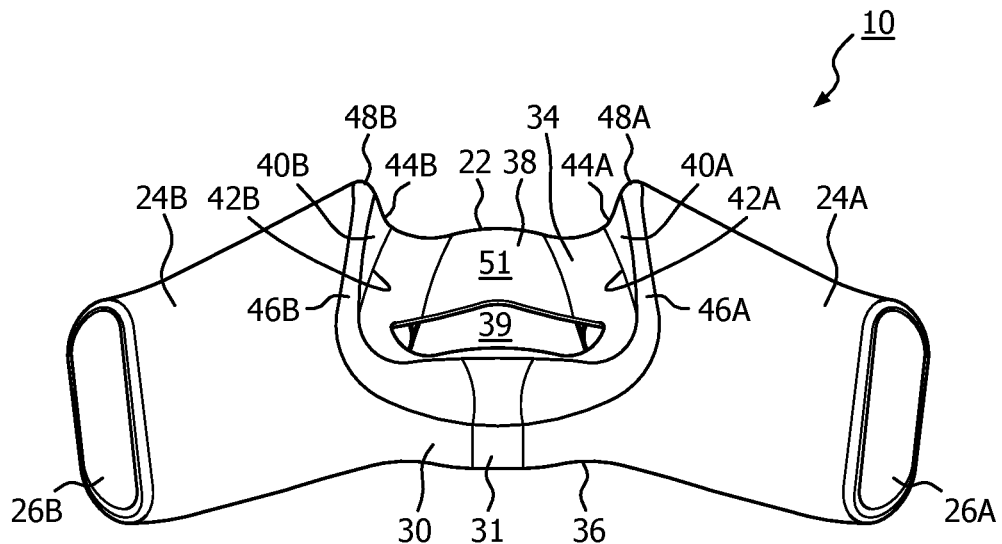
FIG. 5 is a rear elevational view.
Figure 6:
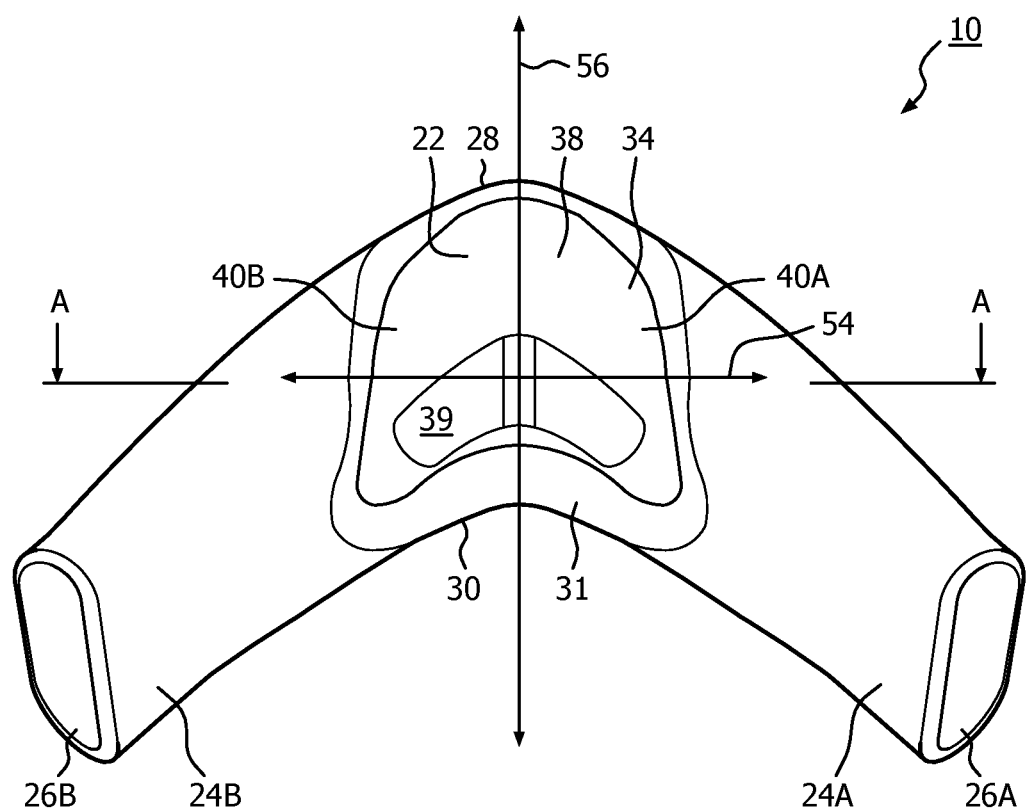
FIG. 6 is a top plan view of a cradle style sealing cushion according to an exemplary embodiment of the present invention that may be employed in a patient interface device of the system of FIG. 1.

FIG. 2 is a front isometric view, FIG. 3 is a front elevational view, FIG. 4 is a side elevational view, FIG. 5 is a rear elevational view, and FIG. 6 is a top plan view of cradle style sealing cushion 10 according to an exemplary embodiment of the present invention. In the exemplary embodiment, cradle style sealing cushion 10 is defined from a unitary piece of soft, flexible, cushiony material, such as, without limitation, silicone rubber, an appropriately soft thermoplastic elastomer, a fabric, or any combination of such materials. It will be understood, however, that cradle style sealing cushion 10 does not need to be unitary within the scope of the present invention. Rather, cradle style sealing cushion 10, and the parts thereof, may be made of separate components that are coupled to one another by suitable means.

Cradle style sealing cushion 10 includes a central sealing body portion 22 defining an internal chamber, a first port portion 24A provided on and extending from a first side of central sealing body portion 22, and a second port portion 24B provided on and extending from a second, opposite side of central sealing body portion 22. First port portion 24A and second port portion 24B are fluidly coupled to the internal chamber of central sealing body portion 22. First port portion 24A includes a first opening 26A and is structured to be fluidly coupled to first arm 14A, while second port portion 24B includes a second opening 26B and is structured to be fluidly coupled to second arm 14B.

Central sealing body portion 22 includes a front side 28 including a front wall 29 and a rear side 30 opposite front side 28 and including a rear wall 31. A plurality of exhaust holes 32 are provided in front wall 29 and act as an exhaust port for patient interface device 8. Exhaust holes 32 may be directed in any direction (or combination of directions) including directly away from the wearer (as shown in the illustrated embodiment), up towards the top of the wearer's head, down towards the wearer's chin, or to the sides. Alternatively, an exhaust port in the form of a semi-permeable porous material, such as a woven fabric, may be provided in place of exhaust holes 32. Central sealing body portion 22 also includes a top wall 34 and bottom wall 36 opposite top wall 34.

Top wall 34 includes a central sealing surface 38 including a hole 39 (providing access to the internal chamber of central sealing body portion 22), and first and second stabilizing surfaces 40A and 40B. In the exemplary embodiment, central sealing surface 38 is structured to engage and form a seal against a septum and a bottom of each nostril of a patent (and possibly the portion of the patient's mouth above the upper lip in one particular embodiment) when the patient interface device is donned by the patient. In addition, first and second stabilizing surfaces 40A and 40B extend upwardly and outwardly from central sealing surface 38 (and the top edge of front wall 29) in a direction away from bottom wall 36 (and the top edge of front wall 29), and are structured to wrap around and, at portions thereof, contact the outer sides (transverse to the bottom) of the nostrils (the alare) of the patient when patient interface device 8 is donned by the patient.

As seen in FIGS. 2 and 3, in the exemplary embodiment, the junction of first and second stabilizing surfaces 40A and 40B with central sealing surface 38 each comprises a rounded, filleted portion (forming a part of first and second stabilizing surfaces 40A and 40B in the exemplary embodiment) which in each case provides a smooth transition between the two surfaces. In addition, first stabilizing surface 40A and second stabilizing surface 40B are provided between the top edge of front wall 29 and the top edge of rear wall 31. In the exemplary, non-limiting embodiment, first stabilizing surface 40A has a generally triangular shape including a base portion 42A, a front side edge portion 44A, a rear side edge portion 46A, and an apex portion 48A. Similarly, in the exemplary, non-limiting embodiment, second stabilizing surface 40B also has a generally triangular shape including a base portion 42B, a front side edge portion 44B, a rear side edge portion 46B, and an apex portion 48B.

Thus, as seen most readily in FIG. 3, the top edge of front wall 29, front side edge portion 44A and front side edge portion 44B together define a front opening 50 of central sealing body portion 22 which exposes the front and top of the patient's nose (i.e., the cradle style sealing cushion 10 does not cover the front and top of the patient's nose). The significance of this feature is described elsewhere herein. Also, the top edge of rear wall 31, rear side edge portion 46A and rear side edge portion 46B together define a rear opening 51 of central sealing body portion 22 that is structured to receive the patient's nose therethrough. In alternative embodiments, first and second stabilizing surfaces 40A, 40B may have other shapes, such as generally rectangular or trapezoidal shapes.

Moreover, as seen in FIG. 3, cradle style sealing cushion 10 has a transverse axis 52 that is a line of symmetry for cradle style sealing cushion 10. Transverse axis 52 is perpendicular to a longitudinal axis 54 of central sealing body portion 22, shown in FIGS. 3 and 4. In addition, as shown in FIG. 6, a center line 56 of central sealing surface 38 extends through the middle of central sealing surface 38 from the center of front side 28 (and front wall 29) to the center of rear side 30 (and rear wall 31). Center line 56 lies in and defines a sealing plane of cradle style sealing cushion 10. In the non-limiting, exemplary embodiment, the sealing plane of cradle style sealing cushion 10, when viewed from the front as shown in FIG. 3, is not orthogonal to transverse axis 52, but instead is angled and extends/slopes downwardly from front to back at an angle of slightly more than zero to thirty degrees with respect to a line or axis that is orthogonal to transverse axis 52.

Figure 7:
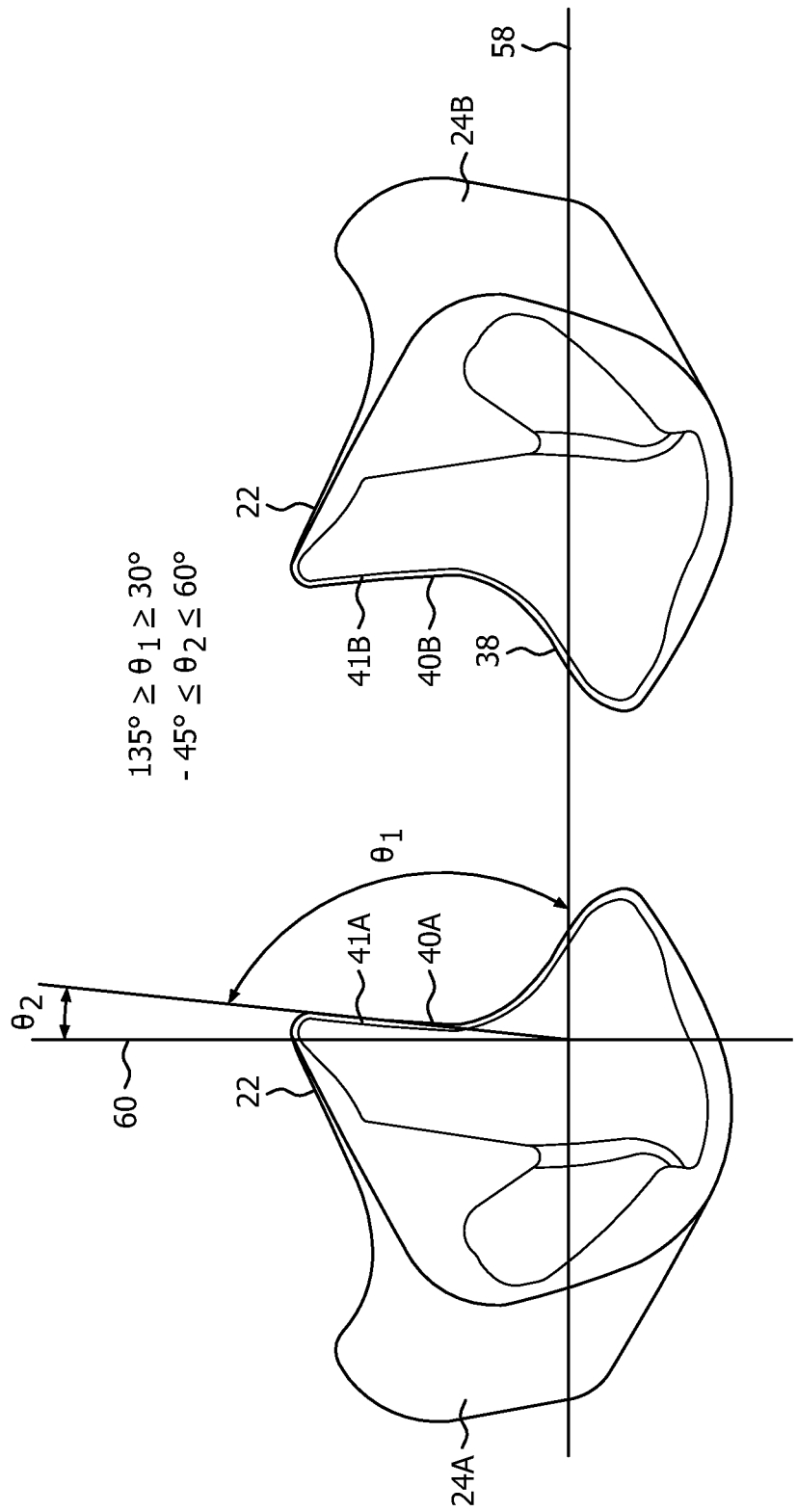
FIG. 7 is a cross-sectional view of cradle style sealing cushion taken along lines A-A of FIG. 6.
Figure 8:
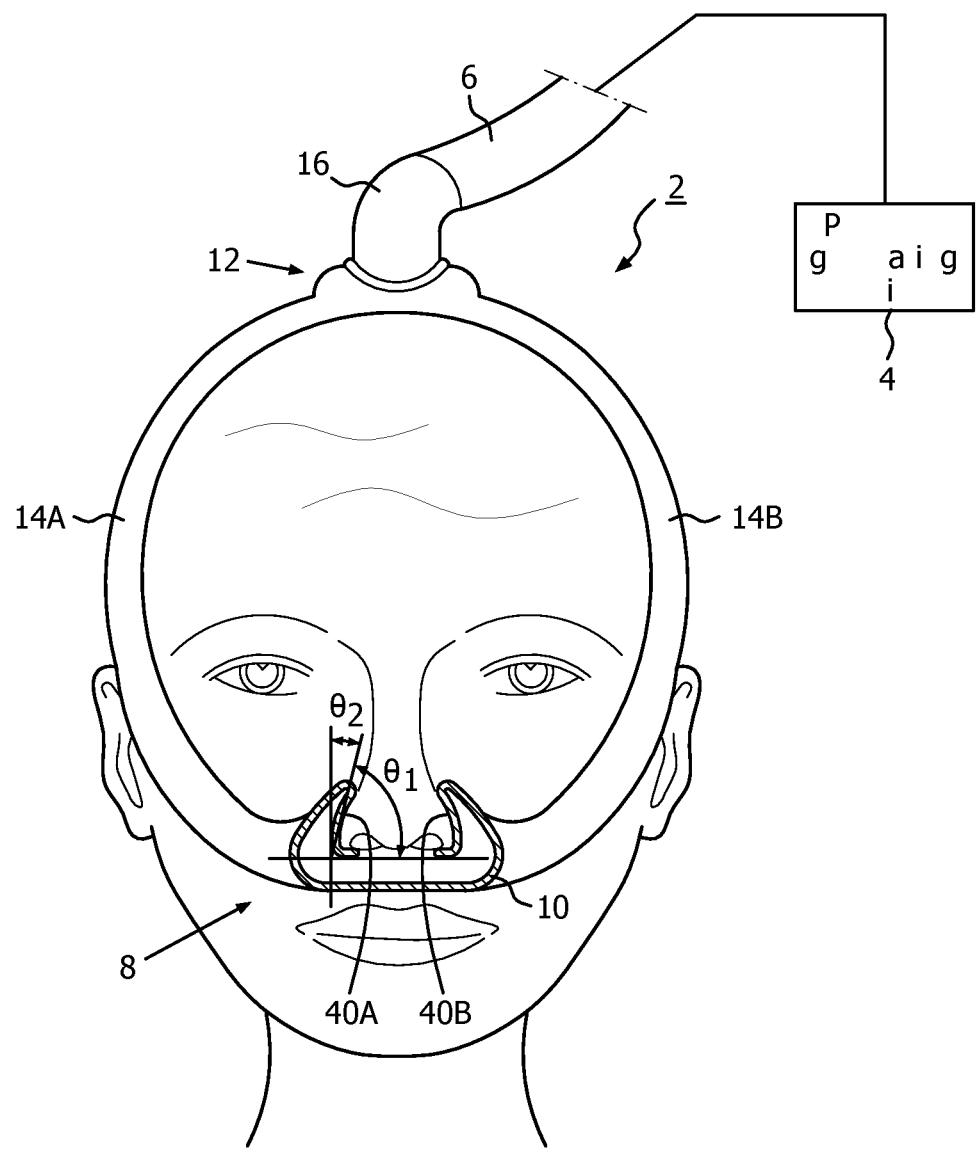
FIG. 8 is a schematic diagram of the system of FIG. 1 wherein the cradle style sealing cushion is shown in cross-section.

In another, exemplary embodiment, the sealing plane of cradle style sealing cushion 10, when viewed from the front as shown in FIG. 3, is a orthogonal to transverse axis 52. In still another, exemplary embodiment, central sealing surface 38 is not flat, but rather actually has an arc where the apex is not necessarily at the front edge but rather closer to the middle of central sealing surface 38. These axes, lines and planes help to define another important feature of cradle style sealing cushion 10. In particular, first and second stabilizing surfaces 40A and 40B each include a contacting portion 41A, 41B that is structured to engage the outside of the nostrils (the alare) of the patient when patient interface device 8 is donned by the patient. In the exemplary embodiment, at any point along the surface of contacting portions 41A and 41B, contacting portions 41A and 41B are configured to lie at an angle $\theta_1$ (FIGS. 7 and 8) (which may be constant or vary within contacting portions 41A and 41B) with respect to the sealing plane (labeled 58 in FIG. 7) of cradle style sealing cushion 10 that is less than or equal to 135 degrees and greater than or equal to 30 degrees. In one particular exemplary embodiment, at any point along the surface of contacting portions 41A and 41B, contacting portions 41A and 41B are configured to lie at an angle $\theta_1$ with respect to sealing plane 58 that is less than or equal to 90 degrees and greater than or equal to 30 degrees. A complementary angle $\theta_2$ is also shown in FIG. 7, wherein $\theta_2$ is measured with respect to a plane 60 that is orthogonal to sealing plane 58 and is less than or equal to 60 degrees and greater than or equal to −45 degrees (less than or equal to 60 degrees and greater than or equal to 0 degrees in the particular exemplary embodiment).

In the exemplary embodiment, the distance between contacting portions 41A and 41B is 25 mm to 55 mm.

Figure 9:
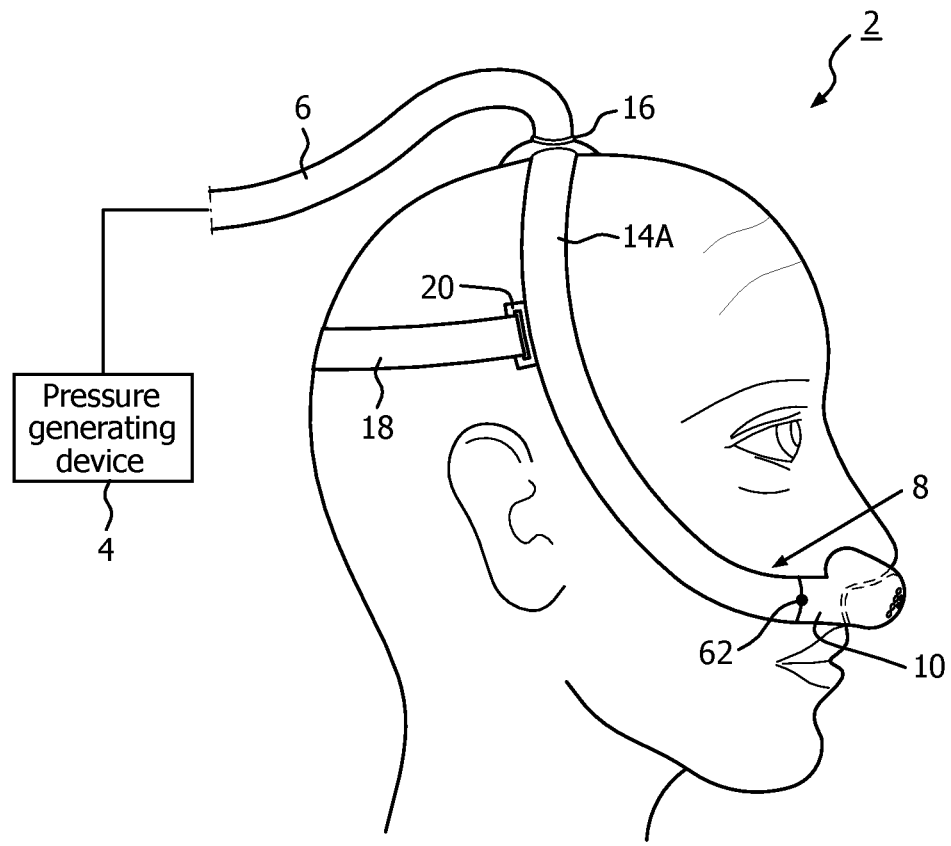
FIGS. 9 and 10 are schematic diagrams of the system of FIG. 1 illustrating the effect of gravitational or similar forces on the patient interface device.
Figure 10:
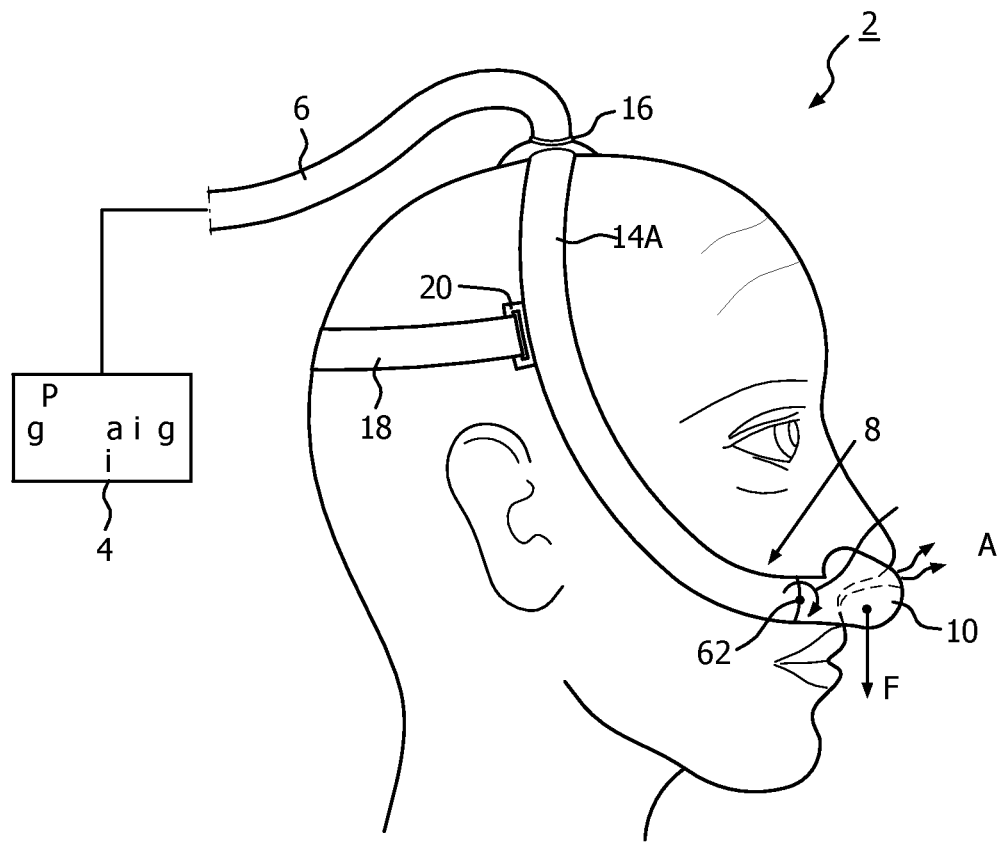

The combination of the side stabilizing features comprising first and second stabilizing surfaces 40A and 40B and the open front (opening 50) serves to direct any air leakage away from the wearer, while blocking the flow of air leakage from the sides of cradle style sealing cushion 10. In particular, as seen in FIGS. 9 and 10, headgear attachment points 62 serve to anchor cradle style sealing cushion 10 to the face, but an external force (e.g. gravity) of sufficient magnitude could cause cradle style sealing cushion 10 to rotate about this anchor point (FIG. 10). With reference to FIG. 10, the cradle style sealing cushion 10 is blocked by the patient's nose from rotating in a counter-clockwise direction, but could potentially rotate clockwise away from the nose. In this situation, the seal adjacent to the face would be maintained, blocking air from jetting into the face of the wearer, while the open front of cradle style sealing cushion 10 (opening 50) facilitates air flow away from the wearer, thereby minimizing discomfort.

Figure 11:
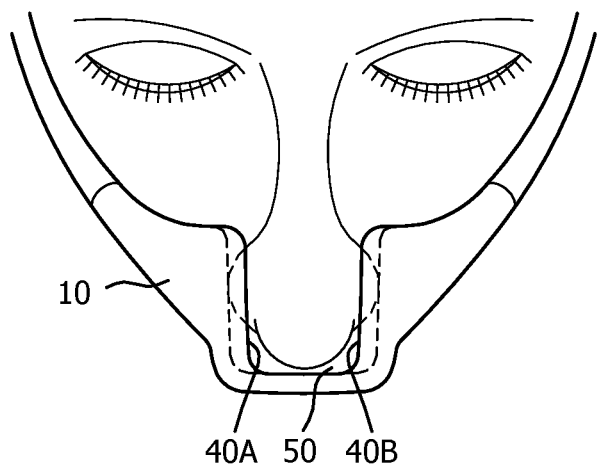
FIGS. 11-13 are schematic diagrams of alternative cradle style sealing cushions that may be employed in a patient interface device of the system of FIG. 1.
Figure 12:
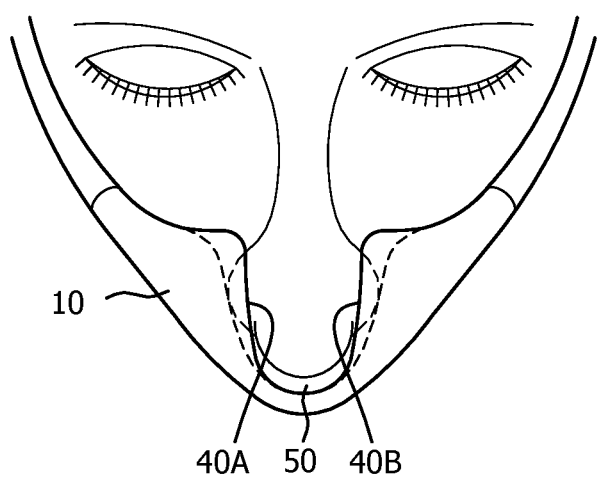
Figure 13:
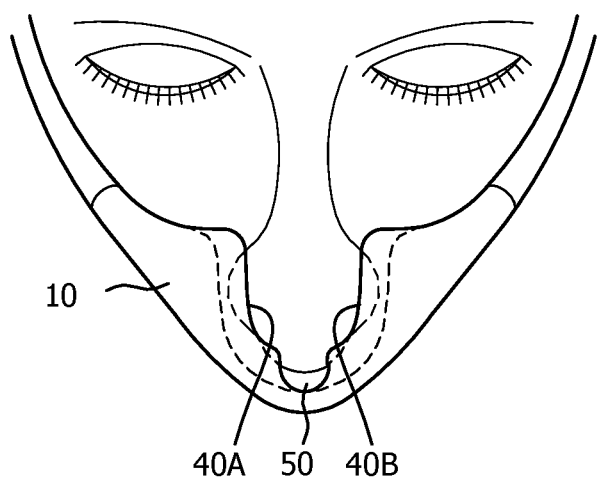

FIGS. 11-13 show cradle style sealing cushions 10', 10" and 10'" according to alterative embodiments wherein first and second stabilizing surfaces 40A', 40A", 40A'" and 40B', 40B", 40B'" thereof curve around toward the nose tip to varying degrees while still maintaining a front opening 50', 50", 50'". Maintaining a wider front opening may help to accommodate noses of extreme length, while maintaining a narrower opening may offer increased stability due to the corresponding larger stabilizing surfaces.

Figure 14:
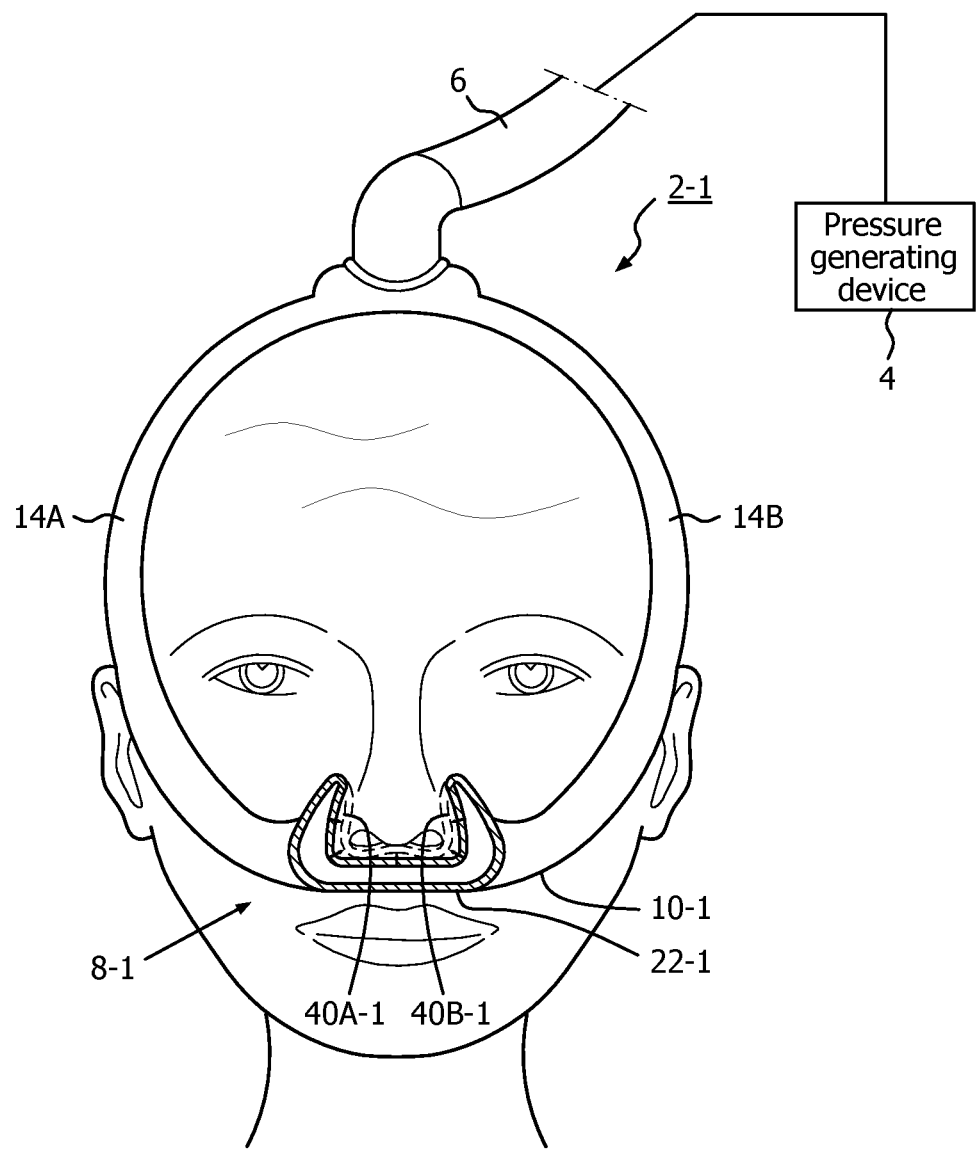
FIG. 14 is a schematic diagram of a system adapted to provide a regimen of respiratory therapy to a patient according to another exemplary embodiment of the invention.

In the embodiments of FIGS. 1-13, cradle style sealing cushions 10, 10', 10" and 10'" are shown and described in a resting, non-inflated/non-deformed state (i.e., without pressurized gas therein). FIG. 14 shows an alternative system 2-1 having an alternative cradle style sealing cushion 10-1 wherein in a resting, non-inflated/non-deformed state, first and second stabilizing surfaces 40A-1 and 40B-1 thereof may or may not satisfy the angular specifications ($\theta_1$ and $\theta_2$) described herein with respect to cradle style sealing cushion 10, but wherein in an inflated/deformed state (responsive to an internal pressure of 4-30 cmH$_2$0), cradle style sealing cushion 10-1 will expand (see arrows in FIG. 14) and first and second stabilizing surfaces 40A-1 and 40B-1 thereof will be caused to satisfy the angular specifications ($\theta_1$ and $\theta_2$) described herein with respect to cradle style sealing cushion 10 and will be caused to engage the outside of the patient's nostrils. Additionally, the cradle style sealing cushions described herein could be constructed of a very soft material (e.g., soft silicone, a gel, or a visco-foam) that could be deformed by contact with the facial anatomy such that first and second stabilizing surfaces 40A-1 and 40B-1 thereof will be caused to satisfy the angular specifications ($\theta_1$ and $\theta_2$) described herein with respect to cradle style sealing cushion 10 (in the resting state, those condition may or may not be satisfied).

Figure 15:
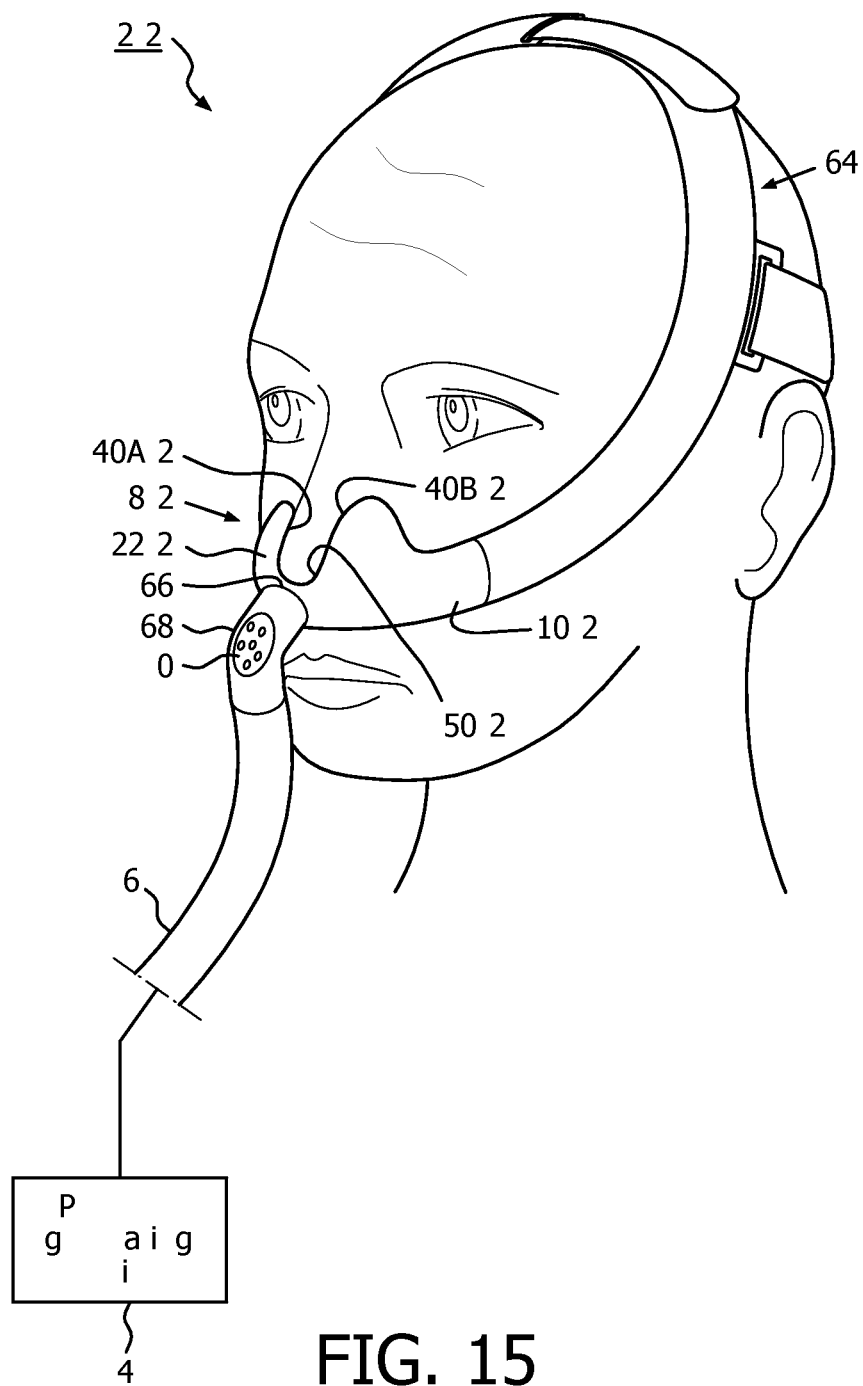
FIG. 15 is a schematic diagram of a system adapted to provide a regimen of respiratory therapy to a patient according to yet another exemplary embodiment of the invention.

A system 2-2 adapted to provide a regimen of respiratory therapy to a patient according to an alternative exemplary embodiment of the invention is generally shown in FIG. 15. System 2-2 includes a pressure generating device 4 and a delivery conduit 6 as described elsewhere herein. System 2-2 includes an alternative patient interface device 8-2. Patient interface device 8-2 comprises a cradle style nasal mask structured to engage the nose of the patient that includes a cradle style sealing cushion 10-2 that is similar to cradle style sealing cushion 10. More specifically, cradle style sealing cushion 10-2 includes a central sealing body portion 22-2 defining an internal chamber that is similar in structure to central sealing body portion 22 in that it includes first and second stabilizing surfaces 40A-2 and 40B-2 having contacting portions that satisfy the angular specifications ($\theta_1$ and $\theta_2$) described herein with respect to cradle style sealing cushion 10 and a front opening 50-2 similar in structure to front opening 50. However, rather than having port portions 24A, 24B that are coupled to tubing assembly 12, the sides of cradle style sealing cushion 10-2 are coupled (not fluidly) to the arms of headgear assembly 64. In addition, the front of central sealing body portion 22-2 is provided with an orifice 66 that provides access to the inner chamber of central sealing body portion 22-2. An elbow conduit 68 having an exhaust port 70 is fluidly coupled to both central sealing body portion 22-2 through orifice 66 and to delivery conduit 6 so that pressured gas from pressure generating device 4 may be supplied to the inner chamber of central sealing body portion 22-2, and then to the airways of the patient.

Figure 16:
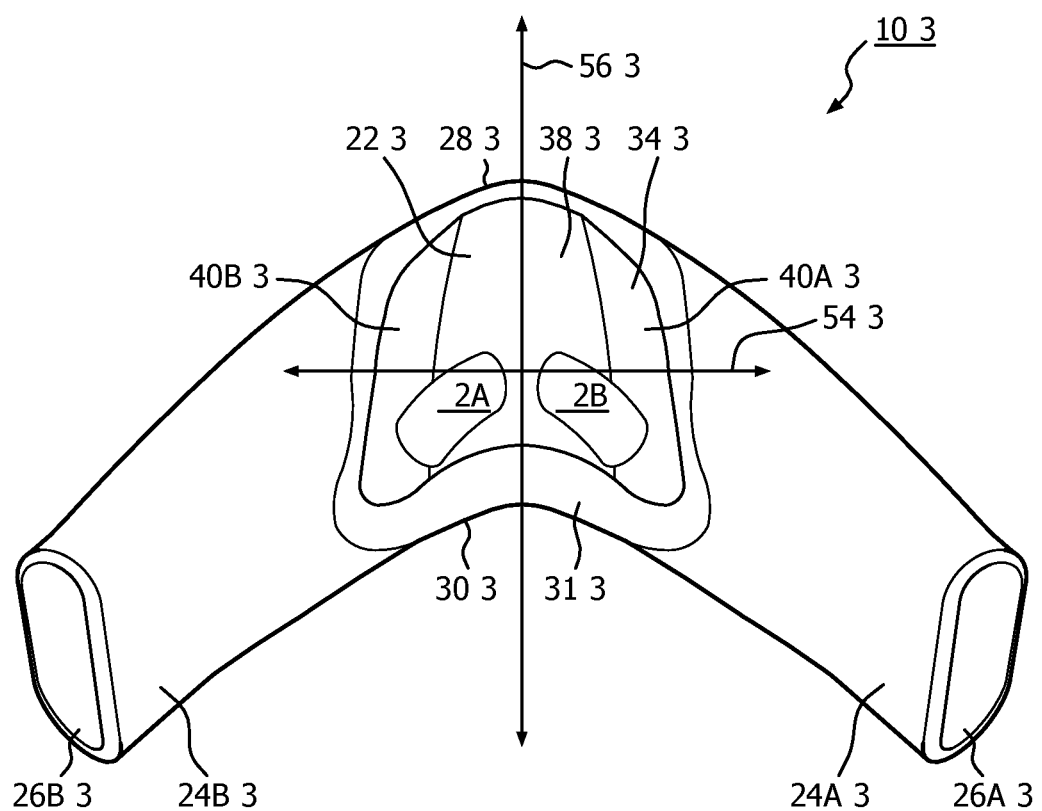
FIG. 16 is a top plan view of a cradle style sealing cushion according to an alternative exemplary embodiment of the present invention that may be employed in a patient interface device of the system of FIGS. 1.

FIG. 16 is a top plan view of a cradle style sealing cushion 10-3 that is similar to (and may be substituted for) cradle style sealing cushion 10 (like parts are labeled with like reference numerals including a "-3" designation). However, rather than including a top wall 34 that includes a central sealing surface 38 including a single hole 39, cradle style sealing cushion 10-3 includes a top wall 34-3 that includes a central sealing surface 38-3 including a first hole 72A and a second hole 72B, wherein each hole 72A, 72B is structured to be aligned with a respective nostril of the patient.

Figure 17A:
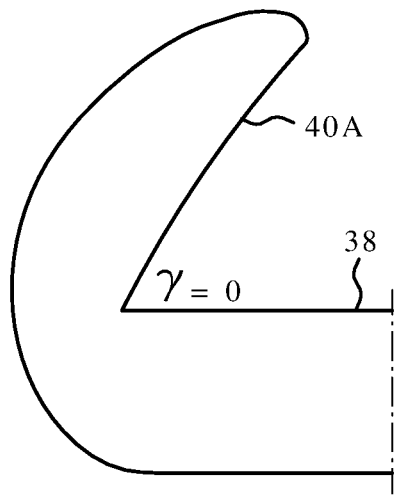
FIGS. 17A, 17B and 17C are schematic diagrams of a cradle style sealing cushion according to another alternative exemplary embodiment of the present invention that may be employed in a patient interface device of the system of FIG. 1.
Figure 17B:
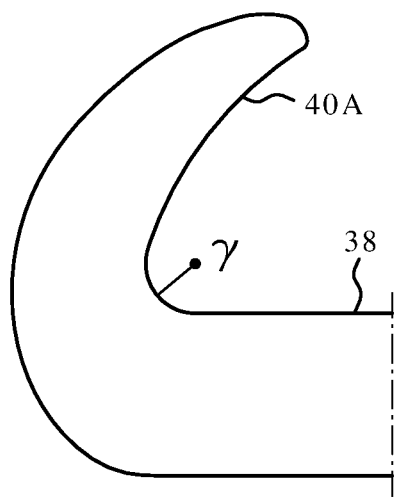
Figure 17C:
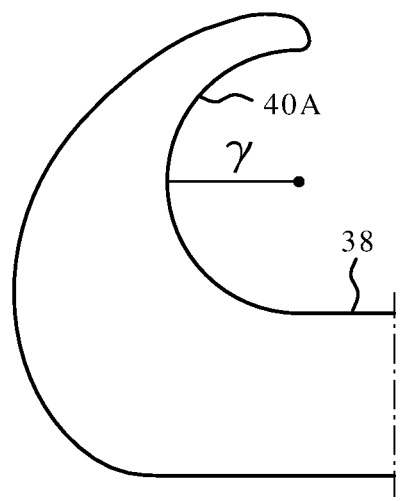

Furthermore, according to yet another embodiment of the present invention, the first stabilizing surface (40A, 40A', 40A", 40A''', 40A-1, 40A-2, 40A-3) and the second stabilizing surface (40B, 40B', 40B", 40B''', 40B-1, 40B-2, 40B-3) (including the transition between the central sealing surface and such side stabilizing surfaces) each include at least a portion wherein the radius of curvature has a certain minimum value that is within a pre-defined minimum range. In the exemplary embodiment, that range is 0 mm to 15 mm. This embodiment is shown schematically in FIGS. 17A, 17B and 17C (using stabilizing surface 40A), wherein in FIG. 17A, the portion has a radius of curvature r that is equal to 0 (the rest of the stabilizing surface is flat with r equal to infinity), wherein in FIG. 17B, the portion has a radius of curvature r that is equal to about 3 mm (the rest of the stabilizing surface has a radius of curvature r equal to about 300 mm), and wherein in FIG. 17C, the portion comprises the entire stabilizing surface and has a radius of curvature r that is equal to about 15 mm.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cradle style cushion for a patient interface device, the cradle style cushion comprising:
    a central sealing body portion defining an internal chamber, the central sealing body portion comprising:
        a front wall,
        a rear wall,
        a bottom wall, and
        a top wall including:
            a flat or concave central sealing surface structured to engage a septum and a bottom of each nostril of a patient when the patient interface device is donned by the patient, the central sealing surface having at least one hole defined therethrough,
            a first stabilizing surface, and
            a second stabilizing surface, the first and second stabilizing surfaces each extending upwardly and outwardly from the central sealing surface and a top edge of the front wall in a direction away from the bottom wall and being structured to wrap around and at portions thereof engage an outer side of a respective one of the nostrils of the patient when the patient interface device is donned by the patient,
        wherein the first stabilizing surface includes a first front side edge portion and the second stabilizing surface includes a second front side edge portion, and wherein the top edge of the front wall, the first front side edge portion and the second front side edge portion together define a front opening of the central sealing body portion which is structured to expose the front and top of the nose of the patient when the patient interface device is donned by the patient, wherein at least a portion of the first stabilizing surface curves inwardly toward a middle of the central sealing surface and has a first radius of curvature of 0 mm to 15 mm and wherein at least a portion of the second stabilizing surface curves inwardly toward the middle of the central sealing surface and toward the first stabilizing surface and has a second radius of curvature of 0 mm to 15 mm.

2. The cradle style cushion of claim 1, wherein a center line of the central sealing surface extends through a middle of the central sealing surface from a center of the front wall to a center of the rear wall, wherein the center line lies in and defines a sealing plane of the cradle style sealing cushion, wherein the first stabilizing surface includes a first contacting portion that is structured to engage the outside of a first one of the nostrils when the patient interface device is donned by the patient, wherein the second stabilizing surface includes a second contacting portion that is structured to engage the outside of a second one of the nostrils when the patient interface device is donned by the patient, and wherein at any point along a surface of each of the first and second contacting portions, the first and second contacting portions are each configured to lie at an angle with respect to the sealing plane that is less than or equal to 135 degrees and greater than or equal to 30 degrees.

3. The cradle style cushion of claim 2, wherein at any point along the surface of each of the first and second contacting portions, the first and second contacting portions are each configured to lie at an angle with respect to the sealing plane that is less than or equal to 90 degrees and greater than or equal to 30 degrees.

4. The cradle style cushion of claim 3, wherein at any point along the surface of each of the first and second contacting portions, the first and second contacting portions are each configured to lie at an angle with respect to the sealing plane that is less than or equal to 90 degrees and greater than or equal to 30 degrees when the cradle style cushion is in a resting state and is not filled with a pressurized gas of 4-30 cmH.sub.20.

5. The cradle style cushion of claim 3, wherein at any point along the surface of each of the first and second contacting portions, the first and second contacting portions are each configured to lie at an angle with respect to the sealing plane that is less than or equal to 90 degrees and greater than or equal to 30 degrees responsive to the cradle style cushion being filled with a pressurized gas of 4-30 cmH.sub.20.

6. The cradle style cushion of claim 3, wherein at any point along the surface of each of the first and second contacting portions, the first and second contacting portions are each configured to lie at an angle with respect to the sealing plane that is less than or equal to 90 degrees and greater than or equal to 30 degrees responsive to the cradle style cushion being deformed by the patient's facial anatomy.

7. The cradle style cushion of claim 1, wherein the first stabilizing surface and the second stabilizing surface are each provided between the top edge of front wall and a top edge of the rear wall.

8. The cradle style cushion of claim 1, wherein the first stabilizing surface has a generally triangular shape including a first base portion, the first front side edge portion, a first rear side edge portion, and a first apex portion, and wherein the second stabilizing surface has a generally triangular shape including a second base portion, the second front side edge portion, a second rear side edge portion, and a second apex portion.

9. The cradle style cushion of claim 1, wherein the at least one hole is only a single hole.

10. The cradle style cushion of claim 1, wherein the at least one hole includes a first hole and a second hole.

11. The cradle style cushion of claim 1, further comprising a first port portion directly connected to and extending directly from the first stabilizing surface, and a second port portion directly connected to and extending directly from the first stabilizing surface, the first port portion and the second port portion being fluidly coupled to the internal chamber of the central sealing body portion, the first port portion including a first opening and the second port portion including a second opening.

12. The cradle style cushion of claim 1, wherein the central sealing body portion is provided with an orifice that provides access to the inner chamber of the central sealing body portion, the orifice being structured to be coupled to an elbow conduit.

13. The cradle style cushion of claim 1, wherein the central sealing surface is structured to engage a portion of the patient's mouth above an upper lip of the patient when the patient interface device is donned by the patient.

14. The cradle style cushion of claim 1, wherein the first stabilizing surface and the second stabilizing surface each have a generally triangular, rectangular or trapezoidal shape.

15. A patient interface device including a cradle style cushion according to claim 1.

16. A system for delivering a flow of breathing gas to a patient, the system comprising: a pressure generating system structured to generate the flow of breathing gas; and a patient interface device fluidly coupled to the pressure generating system, wherein the patient interface device includes a cradle style cushion according to claim 1.

* * * * *